United States Patent [19]

Hui et al.

[11] Patent Number: 5,219,527
[45] Date of Patent: Jun. 15, 1993

[54] SENSOR ELEMENT AND METHOD FOR MAKING THE SAME

[75] Inventors: Henry K. Hui, Laguna Niguel; Charles S. Bankert, Oceanside, both of Calif.

[73] Assignee: Puritan-Bennett Corporation, Carlsbad, Calif.

[21] Appl. No.: 758,291

[22] Filed: Aug. 28, 1991

Related U.S. Application Data

[63] Continuation of Ser. No. 394,638, Aug. 16, 1989, abandoned.

[51] Int. Cl.[5] ............................................. G01N 21/64
[52] U.S. Cl. ................................ 422/82.06; 128/634; 385/13; 422/57; 422/58; 422/82.07; 427/2; 436/68; 436/165; 436/166
[58] Field of Search .................... 422/58, 82.05, 82.07, 422/82.08, 82.06, 57; 385/13; 427/2; 436/68, 165, 166; 128/634

[56] References Cited

U.S. PATENT DOCUMENTS

| Re. 31,879 | 5/1985 | Lubbers et al. ............... 436/133 |
|---|---|---|
| 3,904,373 | 9/1975 | Harper . |
| 4,003,707 | 1/1977 | Lubbers et al. . |
| 4,194,877 | 3/1980 | Peterson ............................ 8/4 |
| 4,200,110 | 4/1980 | Peterson et al. ................ 128/634 |
| 4,344,438 | 8/1982 | Schultz ......................... 128/634 |
| 4,468,229 | 8/1984 | Su ................................. 8/507 |
| 4,557,900 | 12/1985 | Heitzmann ...................... 422/55 |
| 4,568,518 | 2/1986 | Wolfbeis et al. ................ 422/56 |
| 4,657,736 | 4/1987 | Marsoner et al. .............. 422/56 |
| 4,712,865 | 12/1987 | Hsu et al. . |
| 4,824,789 | 4/1989 | Yafuso et al. ................... 436/68 |
| 4,849,172 | 7/1989 | Yafuso et al. ................... 422/55 |
| 4,867,919 | 8/1989 | Yafuso et al. ................... 264/1.5 |
| 4,906,249 | 3/1990 | Fogt et al. ....................... 8/647 |
| 4,919,891 | 4/1990 | Yafuso et al. .............. 422/82.05 X |
| 4,921,589 | 5/1990 | Yates et al. ..................... 204/157 |
| 4,925,268 | 5/1990 | Iyer et al. . |
| 4,999,306 | 3/1991 | Yafuso et al. .............. 422/82.07 X |

FOREIGN PATENT DOCUMENTS

| 0105870A2 | 4/1984 | European Pat. Off. . |
|---|---|---|
| 0283206A2 | 9/1988 | European Pat. Off. . |
| 0336986A1 | 10/1989 | European Pat. Off. . |
| 88/05533 | 7/1988 | PCT Int'l Appl. . |
| 2132348A | 7/1984 | United Kingdom . |

OTHER PUBLICATIONS

The Condensed Chemical Dictionary, 10th Ed., Van Nostrand Reinhold Co, N.Y., pp. 408, 842.

G. G. Vurek; Fiber-Optic Carbon Dioxide Partial Pressure Sensor; Mar. 1983; PB83-189738.

Primary Examiner—Jill A. Johnston
Attorney, Agent, or Firm—Fulwider, Patton, Lee & Utecht

[57] ABSTRACT

A sensor element includes an analyte-permeable matrix which supports and maintains a sensing solution containing an analyte-sensitive indicator substance in a plurality of tiny vesicles. The sensor element is prepared by combining the sensing solution with an emulsifier that renders the solution dispersed within the matrix material. The sensing solution remains suspended in these dispersed vesicles after the matrix solidifies. A sensor element made in accordance with the present invention may be placed at the end of an optical fiber.

8 Claims, 1 Drawing Sheet

SENSOR ELEMENT AND METHOD FOR MAKING THE SAME

This application is a continuation of application Ser. No. 07/394,638, filed Aug. 16, 1989 and now abandoned.

BACKGROUND OF INVENTION

1. Field Of The Invention

The present invention relates generally to instruments for measuring the concentration of elements, compounds and gases in a fluid or gaseous mixture, and more particularly, to a method for homogeneously dispersing an analyte-sensitive indicator substance throughout an analyte-permeable matrix using emulsion-related techniques. The method produces an improved sensor element that is particularly suitable for use with a number of methods and instruments for measuring the content of an analyte in a sample.

2. Description Of The Prior Art

The development of instruments and methods for measuring the concentration of elements and compounds in liquids and gaseous mixtures has been a tremendous breakthrough in many science-related fields, particularly the medical arts. Medical instruments are available for performing in vivo measurements of blood chemistry to determine, for example, pH and the partial pressures of gases, such as carbon dioxide and oxygen, in a patient's blood stream. These instruments use specially adapted catheters, optical fibers and sensor elements that can be placed directly in a blood vessel, muscle, or other bodily tissue of a patient. These implanted devices are generally safe, economical, and can be manufactured from material that permits long term implantation in the body. As a result, physicians can continually monitor the blood chemistry of a patient, eliminating the need to constantly draw blood for laboratory analysis.

Many different forms of analyte-measuring instruments have been designed and developed throughout the years for use in numerous medical and industrial applications. Among the many used methods and instruments are those that rely on optical properties of the sensing element. This process may use a dye made from certain organic substance that is sensitive to a particular analyte. When the dye interacts with the analyte in a liquid or gaseous sample, the dye undergoes a physical change that is directly measurable. This change is usually a physical property of the dye, such as its luminescence or fluorescence intensity or decay time. The change of this physical property is directly related to the concentration of the analyte in the sample.

The analyte-sensitive substance, also called an indicator, is arranged in a sensor element which can be stored in a permeable membrane which allows the analyte to permeate and interact with the indicator while preventing other analytes and fluids from reaching the indicator. The sensor element is usually first placed in the test sample to allow the analyte to interact with the indicator and is then subjected to an external source of excitation, usually a light source, that measures the change in the intensity of the physical characteristic of the indicator. Since the concentration of the analyte is directly related to the difference of intensity, a change in the intensity can be used to calculate the proportion of the analyte present in the sample.

Early devices utilized a monochromatic light beam to determine the intensity of fluorescence of the indicator. These devices used optical lenses and prisms for focusing the monochromatic light onto an external sensing element, or optode, which included a permeable membrane, much like an envelope or bladder, which stored the indicator substance. This membrane acted as a barrier which separated the indicator substance from the fluid being analyzed. While somewhat successful, these early optodes presented a number of problems which hindered performance. For example, these membranes were particularly vulnerable if a slight crack developed either during storage or in use since the indicator would leak out. Also, the indicator had a tendency to leach out of the membrane, especially if the membrane came in contact with a substance having similar properties. As a result of this leakage, the character of the indicator would change and affect the accuracy of any measurement.

The development of glass or optical fibers provided a new source for directing the light source to the sensor element. Optical fiber sensing instruments utilize a relatively similar principle for determining the content of an analyte in a sample. Light generated from an external instrument travels along the optical fiber to the sensor element incorporating the indicator substance which is placed at the distal end of the fiber. The light is then transmitted back from the sensing element to an external detection instrument that measures the change of intensity of the indicator.

Other optical systems utilize multiple optical fibers and a sensor element that is remotely located on a catheter or similar device. These systems include at least one light transmitting optical fiber which is placed in close alignment with the remote sensor element and a second output fiber that carries the irradiated light from the sensor to the external detection instrument.

The use of optical fibers required the development of new sensor elements that could be contained in a compact geometry. These elements had to be, of course, much smaller than the conventional bladder-type optode. Also, due to the thin diameter of the fiber, the use of bladders or envelops were generally not feasible due to their relatively large size. Some bladder retaining sensors were developed, but suffered from the same leaking and leaching problems that confronted the earlier optodes.

Alternative solutions for creating a usable sensor included dispersing particles containing an indicator in an analyte-permeable matrix. These sensor proved to be much smaller than conventional optodes, but they too had similar problems of leaching and were vulnerability to cracks that allow the indicator to leak from the matrix. Also, the size of these sensors were directly subject to the thickness of the largest indicator containing particle. Other disadvantages included uneven distribution of the indicator throughout the matrix which caused variations between sensors made from similar materials.

Accordingly, those concerned with the development and use of optical fiber sensing devices have recognized the need for improving the sensor element which contains the indicator substance. Preferably, an improved sensor element should be capable of easy application to an optical fiber and should be capable of being manufactured in a thin profile. The sensor element should have an even dispersal of the indicator throughout the permeable membrane and should not be vulnerable to small cracks that could render the sensor useless. Further-more, it would be extremely advantageous if such a sensor element could be used with a variety of analyte measuring systems and capable of being applied to the optical fiber in one manufacturing step.

SUMMARY OF THE INVENTION

The present invention provides a sensor element and a method for making the same in which sensing solution including an analyte-sensitive indicator is dispersed in tiny vesicles that are supported within an analyte-permeable matrix. The method utilizes techniques in emulsion technology to form the vesicles within the permeable matrix. The sensing solution is initially mixed with an emulsive substance that renders the sensing solution immiscible with the material that makes up the matrix. Both the sensory solution and the matrix material are added together in liquid form. Due to the presence of the emulsifier, the sensing solution will not blend with the matrix material and will be "suspended" in tiny vesicles throughout the matrix material. When the matrix material solidifies, the sensing solution remains suspended within the matrix in liquid form.

The resulting structure provides a sensor element in which the cured matrix serves to support the vesicles of sensing solution in addition to selectively transmitting the desired analyte and isolating the sensing solution from the sample solution. The structure also provides a sensor element that should remain substantially unimpaired should a slight crack develop in the matrix during use or in storage. In the event that a slight crack does develop, the matrix will expose sensing solution in only a small number of vesicles leaving the majority of vesicles unimpaired and ready for use. The result is a superior sensor element that can be used over and over again even if one or more cracks develops in its structure. Similar cracks in prior art sensors would render most unusable.

The size of each vesicle can also be quite small to allow the sensor element to manufactured in an extremely thin profile. The size of the vesicle will depend on how well the sensing solution is dispersed in the liquid matrix material. The sensing solution can, for example, be mixed with high shear into the matrix to increase the number of vesicles while reducing their size. Alternatively, if larger vesicles are desired, the matrix need not be mixed as rapidly with the sensing solution to reduce the number of vesicles thereby increasing their size. In this fashion, the mixture of the sensory solution with the matrix can be directly varied to increase or decrease the size of the vesicles.

In one form of the present operation, the sensor element is made with a matrix that has a thickness that is only slightly larger then the size of the smallest vesicle. Such a sensor will provide sufficient exposure of the indicator within the matrix and will result in an ultra thin profile.

The sensor element can be directly applied onto the end of an optic fiber or it can be manufactured as a separate element that can be used with existing or larger size measuring instruments that utilize external optodes. The invention also provides several important benefits over prior art sensors since the sensor solution and the matrix can be applied to the optical fiber in one manufacturing step. This improves the manufacturing of the sensor since the number of assembly steps is reduced. Also, variations between different sensors decreases due to the homogeneity of the sensor solution within the matrix material.

The matrix can be made from a hydrophobic material which is essentially impervious to ions and water and will transmit sufficient water vapor over time to permit rehydration of the sensor. Sensors manufactured in accordance with the present invention may be stored dry and then rehydrated over a period of several hours. Such a sensor has clear advantages over those prior art sensors which must be kept hydrated throughout the manufacturing and storage periods.

In one form of the invention, the sensor element contains not one, but two, sensing solutions including separate indicators which can be evenly dispersed throughout the matrix. This allows a single sensor element to be used to detect not one, but two or more analytes. Of course, the matrix must be selected from materials that will be permeable to the additional analytes.

From the above, it may be seen that the present invention provides a new and useful sensor element and method for preparing the same for detecting the concentration of an analyte(s) in a fluid or gaseous mixture by the use of indicators that are physically responsive to an analyte and can be exposed to an external excitation, such as light to measure the physical response. Other features and advantages of the present invention will become apparent from the following detail description, taken in conjunction with the accompanying drawings, which illustrate, by way of example, the principal of the invention.

DESCRIPTION OF THE PREFERRED EMBODIMENTS

A sensor element and a method for making the same utilizes an analyte-permeable matrix which supports a sensing solution including analyte-sensitive indicator in a plurality of vesicles that are homogenously dispersed throughout the matrix. The structure is an advance over prior art sensors since the sensor is less susceptible to slight cracks that may develop in the matrix. A slight crack only has a minimal affect on the sensor element since only sensing solution from a small number of vesicles will be released while the majority of vesicles will remain intact and capable of functioning normally.

The present invention utilizes techniques of emulsion technology to form the vesicles within the matrix. The sensing solution is specifically mixed with an emulsifier that prevents the solution from "blending" with the liquified matrix material when the two compounds are initially mixed. The sensing solution and the matrix material must be made from mutually immiscible compounds that cause the sensing solution to be "suspended" in the tiny vesicles in the liquified matrix material. The sensor solution can be homogenized with the liquified matrix material to reduce the size of the tiny vesicles and for more even dispersement. The matrix material is allowed to solidify with the sensing solution still suspended within its structure. The resulting structure creates a sensing element which provides ample exposure of the analyte-sensitive indicators to an external source excitation, such as a beam of light.

Sensor elements which are used to determine the concentration of an analyte in a fluid or gaseous mixture are well known in the art. Many of these sensors utilized an external source of a light excitation having a certain wavelength which measures the physical change of the indicator after it is interacted with the analyte. The indicator is irradiated with the light and its physical change is measured for calculating the concentration of the analyte in the test sample.

Figure 1:
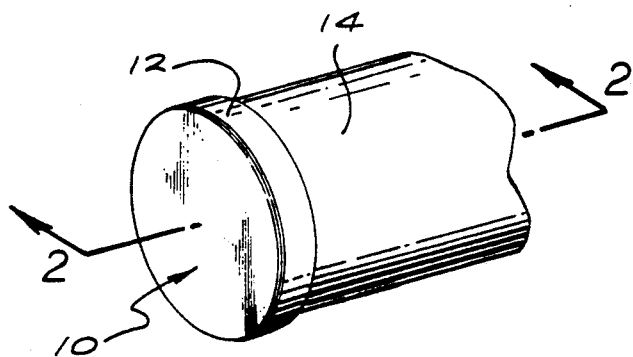
FIG. 1 is a perspective view of a sensor element made in accordance with present invention as it is affixed to the end of an optical fiber.

FIG. 1 illustrates a general arrangement of a sensor element 10 made in accordance with the present invention as it is affixed to a free end 12 of an optical fiber 14. This sensor element 10 and a fiber 14 are specifically designed for use with measuring instruments that utilize a light source for measuring the change of intensity of the fluorescence of analyte-sensitive dye. Generally, the sensor and the fiber are placed in a sample of fluid or gaseous mixture which contains a certain concentration or content of the analyte that is desired to be measured. Alternatively, due to their small size, the sensor and optical fiber can be easily placed within a blood vessel, tissue or muscle of a patient for in vivo measurement of the analyte.

Figure 2:
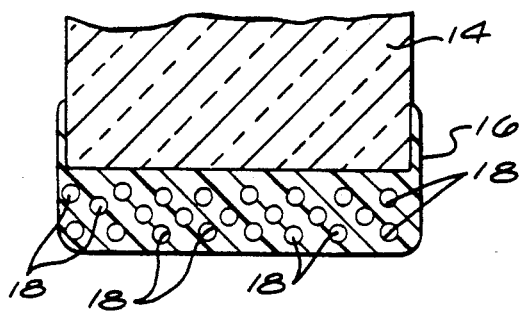
FIG. 2 is an enlarged cross-sectional view of the sensor element shown in FIG. 1 and taken along line 2—2.

Referring to FIG. 2, this sensor element 10 includes a matrix 16 through which a plurality of vesicles 18 are homogenously dispersed. Each of these vesicles contains a minute amount of sensing solution including an indicator substance that is sensitive to the analyte being measured. These vesicles 18 are thoroughly dispersed within the matrix 16 to insure that a sufficient amount of indicator substance is exposed within the matrix and to the irridating light source that will be transmitted through the optical fiber.

The matrix 16 is made from a material that is selectively permeable to the particular analyte that is being measured. The matrix acts much like a protective barrier which separates the sensing solution from the fluid or gas mixture that is being analyzed, allowing only the desired analyte to permeate to the sensing solution while preventing other fluids and gases from reaching the solution.

In use, light of a certain wavelength is transmitted to the optical fiber 14 from an external instrument (not shown). The light irridates the encapsulated indicator substance and is transmitted back to an external instrument (not shown) that measures the intensity of the fluorescence of the indicator. In this manner, the measure of the intensity can be used to calculate the concentration of the analyte in the sample. Since the indicator is well dispersed throughout the sensor element, the difference in the intensity of the light attributable to the presence of the analyte will be an accurate measure of the concentration in the sample.

The benefits of utilizing numerous vesicles in the matrix become apparent if a slight crack should develop in the sensor element during use or while the element is in storage. A slight crack will only expose the sensing solution in a small number of vesicles, leaving the majority of vesicles essentially unimpaired and capable of performing their designed function. As a result, the present invention can still be used over and over again even if cracks develop within the matrix.

The size of the vesicles also determines the thickness in which the sensor element can be manufactured. During the mixing of the sensing solution with the liquified matrix material, the size of the vesicles of the sensing solution can be varied depending upon the rate at which the solution is "mixed" with the matrix material. For instance, if smaller vesicles are desired, then the sensing solution must be vigorously mixed with the matrix to decrease the size of the vesicles. This also increases the number of vesicles as well. If larger vesicles are required, then the intensity of the mix between sensing solution and matrix material would have to be reduced. Correspondingly, when the size of the vesicles are increased, the number of them decreases.

In one embodiment of the present invention, the sensor element can be manufactured having a thickness that is only slightly larger than the size of the smallest vesicle that can be formed within the matrix. This can be a desirable structure in those applications which require certain size limitations for the sensor.

It should be appreciated that the indicator substance is not limited to fluorescent compounds. The sensor may also use an indicator that experiences a change in its absorption, luminescense, or phosphorescence as well, for example. The choice of the indicator substance will depend on the analyte that is being measured and the particular application contemplated for the sensor element.

The matrix can be made from a material that is hydrophobic to protect the integrity of the sensing solution from ionic species in the sample being tested. A typical hydrophobic material that is suitable for use is silicone. Silicone is just one example of a suitable material that can be used for the matrix. Silicone is permeable to a number of gases and is available in a liquid form that can be cross-linked to form a semi-soft solid. The solid silicone matrix is ideal for use since it can be easily mixed with the sensing solution and can be directly applied to an optical fiber that can be dry cured to its solid form. In this fashion, the sensing element can be easily applied to the optical fiber in a single manufacturing step, eliminating the need for other time consuming steps.

Figure 3:
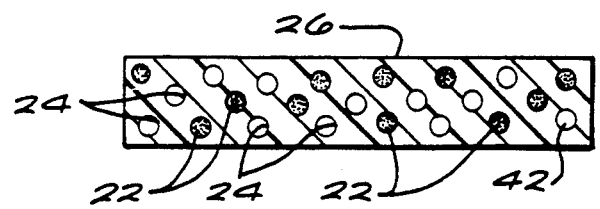
FIG. 3 is a cross-sectional view of another embodiment of a sensor element made in accordance with the present invention which utilizes two sensory solutions for detecting two different analytes.

FIG. 3 shows an alternative embodiment of a sensor element in which two distinct sensing solutions 22 and 24 having different indicator substances are disposed in a plurality of vesicles dispersed throughout the matrix 26. In this form of the invention, the matrix 26 is made from a material that is permeable to the two analytes that are to be tested. Each solution also contains an emulsifier which prevents the solutions from blending with the liquified matrix material when the compounds are added together. Each sensing solution may also be immiscible to each other to prevent the two solutions from blending together as well.

Figure 4:
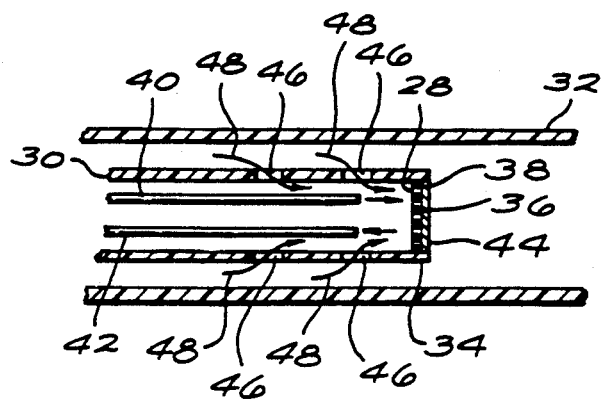
FIG. 4 is a partial cross-sectional side view of a sensor element made in accordance with the present invention that can be used with a multiple optical fiber systems that can be placed in a blood vessel of a patient.

FIG. 4 shows an alternative embodiment of the present invention in which a sensor element 28 is contained within a catheter 30 that is placed in a blood vessel 32 of a patient. This sensing element 28 is located near the distal end 34 of the catheter 30 and is structured as a thin membrane which supports the sensing solution within vesicles 36 formed in a permeable matrix 38. In this particular embodiment, the sensor element is just slightly larger than the size of a vesicle. This enables the analyte to penetrate through the matrix much easier and interact with the analyte-sensitive indicator substance contained within the vesicles.

This particular sensor element is made accessible to a optical fiber 40 which transmits the irradiating light to the sensor 28. A separate optical fiber 42 used to carry the light back to a detection instrument located outside the patient is also utilized. In this particular arrangement, an additional reflector 44 may be placed behind the sensor element 28 to help reflect the irradiating light back to the optical fiber 42. In practice, a single fiber which transmits and returns the irradiating light may be used.

The catheter shown in FIG. 4 includes a number of openings 46 which allow blood to travel and permeate through the matrix. All in all, this embodiment shows the adaptability and versitility of a sensor element built in accordance with the present invention and how it can be modified for use with different measuring systems.

The method for making a sensor element in accordance with the present invention requires the mixing of the sensing solution with an emulsifier agent which renders the solution immiscible with the particular material used to form the matrix and which also stabilizes the resulting dispersion. The emulsified sensing solution can be mixed with the liquified matrix material to allow the formation of the numerous vesicles in the matrix material. The number of vesicles and their size can then be directly varied by changing the intensity in which the solution and matrix materials are mixed. For example, if many vesicles of a small size are desired, then the two compounds must be vigorously mixed together. Conversely, the number of vesicles can be easily decreased by simply decreasing the intensity in which the solution is mixed with the matrix. Regardless of the intensity of the mixture, tiny vesicles containing the sensing solution and indicator are dispersed within the matrix material where they will remain in liquid form after the matrix material cures. Generally, the matrix material is allowed to solidify by a dry air process. In some instances, the matrix material must be cross-linked to form a solid material. In such a case, an appropriate amount of cross-linking agent should be added to the mixture.

The emulsifier used in accordance with the present invention may be a water soluble or water swellable polymer. For example, possible emulsifiers include polyvinylpyrrolidone, polyethylene glycol, and polyethylene oxide.

Before the matrix material solidifies, a specially prepared optic fiber can be dipped into the mixture to form the sensor element at the end of the fiber. Once the fiber is dipped into the mixture, it can be removed and allowed to solidify.

The following example is included for further understanding of the invention. It should be understood that this example is by no way intended to limit the scope of the present invention.

AN EXAMPLE DEMONSTRATING ONE METHOD FOR PREPARING THE SENSOR ELEMENT

The following example illustrates the preparation of a sensor element which can be used to detect an analyte such as carbon dioxide. Initially, five grams of polylvinylpyrrolidone (40,000 mw) were dissolved in an aqueous solution of 0.01M hydroxypyrene trisulfonic acid and 0.1M sodium bicarbonate. A sample of 1.5 grams of the resulting compound was added to 10 grams of Petrarch PS783 silicone. These two components were mixed, utilizing a high speed homogenizer, for one minute at the highest setting. A small aliquot of platinum catalyst (0.005 g) was also added to the homogenized mixture. The mixture was again homogenized for an additional minute at the highest shear rate. A 0.5 gram portion of the resulting mixture was hand mixed with 0.05 g of Petrarch PS123 cross-linker.

The cured compound was placed in a saline solution and 2.64% carbon dioxide bubbled through the solution. When the sample was irradiated with 460 mn light, the emission at 515 nm yielded a normalized voltage of 4.481 on a detector. When the concentration of carbon dioxide was increased to 8.2% carbon dioxide, the resulting normalized voltage was 3.316 V. This indicates a functioning carbon dioxide sensor.

From the above, it is evident that the present invention provides a means for preparing a sensor element that evenly distributes an indicator substance throughout an analyte-permeable matrix. The resulting sensor is superior over prior art devices due to the even distribution of indicator. While particular forms of the invention have been described and illustrated, it will also be apparent to those skilled in the art that various modifications may be made without departing from the spirit and scope of the invention. Accordingly, it is not intended that the invention be limited, except as by the appended claims.

We claim:

1. A sensor element comprising:
   an optical fiber having a distal portion coated with a matrix made from a hydrophobic material that is permeable to at least one analyte;
   a first plurality of vesicles disposed in said matrix containing a first aqueous sensing solution with a first fluorescent dye indicator that is responsive to a particular analyte; and
   a second plurality of vesicles disposed in said matrix containing a second aqueous sensing solution with a second fluorescent dye indicator that is responsive to a second analyte, said vesicles being dispersed throughout said matrix, said matrix being only slightly thicker than the size of one of said vesicles.

2. A sensor element as defined in claim 1 wherein each said sensing solution and the matrix material are mutually immiscible.

3. A sensor element as defined in claim 1 wherein each of said first and second sensing solutions contains an emulsifier that forms an emulsion of said first and second sensing solutions with said matrix, and that renders each of said sensory solutions immiscible with said matrix and stabilizes the resulting emulsion.

4. A sensor element as defined in claim 3 wherein the emulsifier is a water soluble or water swellable polymer.

5. A sensor element as defined in claim 3 wherein the emulsifier is selected from a group consisting of polyvinylpyrrolidone, polytheylene glycol and polyethylene oxide.

6. A method for making a sensor element comprising the steps of:
   combining a first sensing solution including an indicator substance that is responsive to an analyte with an emulsifier solution to form a first emulsified solution;
   mixing a liquified matrix that is immiscible with the first sensing solution, and that is permeable to at least one analyte with the first emulsified solution;

combining a second sensing solution that is immiscible with the liquified matrix and the first sensing solution, and having an indicator that is receptive to a second analyte with an emulsifier to form a second emulsified solution;

mixing the second emulsified solution with the liquified matrix and the first emulsified solution;

dispersing the first and second emulsified solutions as a plurality of vesicles in the liquified matrix material; and causing the liquified matrix to solidify in a thickness only slightly greater than the size of one of said vesicles.

7. The method of claim 6 wherein the first and second emulsified solutions are homogeneously dispersed throughout the matrix.

8. The method of claim 6 further comprising, before the dispersing step, the step of:

mixing a catalyst to the emulsified solutions and liquified matrix.

* * * * *